United States Patent [19]

Castro et al.

[11] Patent Number: 4,865,789

[45] Date of Patent: Sep. 12, 1989

[54] METHOD FOR MAKING POROUS STRUCTURES

[75] Inventors: Anthony J. Castro, Chicago; Dieter Frank, Naperville; Cleve Madlock, Jr., Westmont, all of Ill.

[73] Assignee: Akzo NV, Netherlands

[21] Appl. No.: 551,446

[22] Filed: Nov. 14, 1983

[51] Int. Cl.[4] ............................................. B29C 67/24
[52] U.S. Cl. ................................... 264/122; 264/120; 264/123
[58] Field of Search ............... 264/120, 123, 294, 319, 264/122, 109, 321; 425/345

[56] References Cited

U.S. PATENT DOCUMENTS

| 2,569,226 | 9/1951 | Carter | 264/120 |
| 3,671,157 | 6/1972 | Smith | 425/345 |
| 3,674,722 | 7/1972 | Rainer et al. | 264/109 |
| 4,205,137 | 5/1980 | Akiyama | 264/321 |
| 4,247,498 | 1/1981 | Castro | 264/49 |
| 4,349,542 | 9/1982 | Staniforth | 264/109 |

OTHER PUBLICATIONS

The Packing of Particles, Westman and Hugill Ontario Research Foundation, Toronto, Canada.

Primary Examiner—Jan H. Silbaugh
Attorney, Agent, or Firm—Louis A. Morris

[57] ABSTRACT

A method for making a porous structure including forming a plurality of particles into a desired shape, the particles being in a size range from about 40 to about 400 microns and including from about 5 to about 100 percent by weight of microporous particles of a synthetic thermoplastic polymeric material and from about 0 to about 95 percent by weight of nonporous synthetic thermoplastic polymeric material; and subjecting the particles to an effective pressure from about 200 to about 8000 pounds per square inch, while retaining the particles in the desired shape, for a sufficient length of time to produce an integral porous structure having substantial physical integrity.

9 Claims, 5 Drawing Sheets

METHOD FOR MAKING POROUS STRUCTURES

BACKGROUND OF THE INVENTION

This invention relates to a method for making porous structures and in particular to a method for making microporous structures of a desired shape.

Porous structures are available through a wide variety of processes. However, few processes are capable of producing microporous structures having substantial three-dimensional sizes. One process capable of producing such structures is described in U.S. Pat. No. 4,247,498, which is incorporated herein by reference. Typical processes for making microporous materials, such as classical phase-inversion, are best able to produce structures such as flat sheets. Sintering techniques can produce three-dimensional microporous shapes, but usually such shapes will have a high density and a low void volume.

The process of U.S. Pat. No. 4,247,498, even though it is capable of producing three-dimensional shapes of various sizes, has the drawback that substantial times may be necessary to form such structures due to the slow rate of extraction of the compatible liquid. A need therefore exists for a facile method for making microporous three-dimensional structures of various shapes.

SUMMARY OF THE INVENTION

There has now been discovered a method for making a porous structure comprising forming a plurality of particles into a desired shape, said particles being in a size range from about 40 to about 400 microns and being comprised of from about 5 to about 100 percent by weight of microporous particles of a synthetic thermoplastic polymeric material and from about 0 to about 95 percent by weight of nonporous synthetic thermoplastic polymeric material; and subjecting said particles to an effective pressure from about 200 to about 8000 pounds per square inch, while retaining said particles in said desired shape, for a sufficient length of time to produce an integral porous structure having substantial physical integrity.

DETAILED DESCRIPTION OF THE PREFERRED EMBODIMENT

Figure 1:
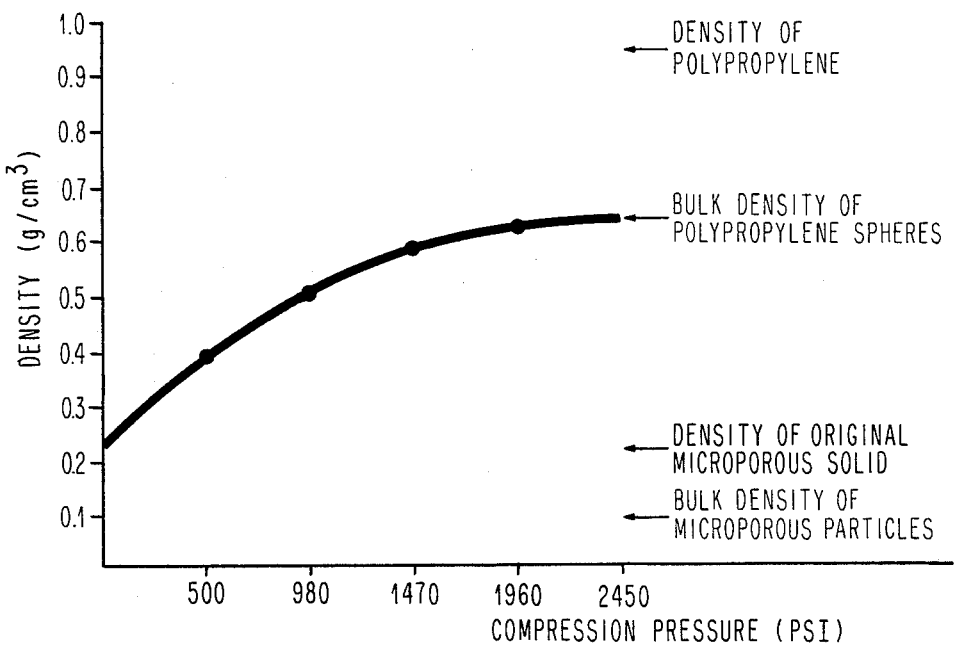
FIG. 1 is a graph showing the resultant density of the structures of the present invention made from microporous polypropylene, as a function of the compressive force used to make the structures.

As indicated, the present method provides a facile means for producing three-dimensional porous structures. By use of the present invention it is possible to produce porous structures with a density less than the theoretical density of an identical structure made solely from nonporous particles of the same material, at the same pressure.

The starting materials are particles of a synthetic polymeric material. The material may be a homopolymer, a copolymer, or a blend of various homopolymers and/or copolymers. The process of the present invention applies to olefinic polymers, condensation polymers, and oxidation polymers. Typically the synthetic polymeric material will be a homopolymer of polypropylene or polyethylene.

Exemplary of the useful non-acrylic polyolefins are low density polyethylene, high density polyethylene, polypropylene, polystyrene, polyvinylchloride, acrylonitrile-butadiene-styrene terpolymers, styrene-acrylonitrile copolymer, styrene butadiene copolymers, poly(4-methyl-pentene-1), polybutylene, polyvinylidene chloride, polyvinyl butyral, chlorinated polyethylene, ethylene-vinyl acetate copolymers, polyvinyl acetate, and polyvinyl alcohol.

Useful acrylic polyolefins include polymethylmethacrylate, polymethyl-acrylate, ethylene-acrylic acid copolymers, and ethylene-acrylic acid metal salt copolymers.

Polyphenylene oxide is representative of the oxidation polymers which may be utilized. The useful condensation polymers include polyethylene terephthalate, polybutylene terephthalate, Nylon 6, Nylon 11, Nylon 13, Nylon 66, polycarbonates and polysulfone.

The nonporous particles which may be employed in one embodiment of the present invention may be obtained by simple grinding and classifying of solid resin of any physical form. Such particles may also be obtained from several commercial sources.

Although the microporous particles may be made by any process which will produce such particles of the desired synthetic polymeric material, it is preferred to use the process of U.S. Pat. No. 4,247,498. An initial structure of any shape may first be made using said process, preferably in a form which is readily made and easily grindable. Such an initial structure may then be cryogenically ground using commercially available equipment for such a purpose and subsequently be extracted. The particles resulting from the structure may then be classified according to the particles size. It is preferable to use particles within the size range of about 40 to about 400 microns.

For the present invention at least 5 percent of the particles employed must be microporous and will preferably have a high void volume, as, for example, from about 50 to about 90 percent, with about 70 to about 80 percent being most preferable. The size of the microporosity is not critical and will usually be in the range from about 0.05 micron to about 5 microns with about 0.2 to about 1.0 micron being more typical.

As indicated, virtually any shape may be employed in the present invention. In particular, tablets or discs may be formed using simple devices to retain the particles in the desired shape. External pressure is applied to the particles, as by using a hydraulic press, such as is used to make KBr tablets for infrared spectroscopy.

The pressure employed may be from about 200 to about 8000 pounds per square inch. Usually significant strength will be obtained when the pressure utilized is about 300 pounds per square inch, or greater. However, as the pressure exceeds about 1500 pounds per square inch and approaches about 2500 pounds per square inch, the density of the resultant structure approaches the theoretical value for the bulk density of nonporous polypropylene spheres in a hexagonal dense pack configuration. It could therefore be assumed that the remaining porosity is mainly the interstitial void space. From Scanning Electron Photomicrographs ("SEMs"), however, it is apparent that the original microporous particles flatten out first thus eliminating the interstitial voids before the micropores start to disappear.

Thus, for example, the remaining porosity of a specimen made at 2100 psi may be 33%, of which a substantial portion is still microporosity and not interstitial space between the spherical particles, which theoretically is 31% in a hexagonal dense pack configuration.

Figure 2:
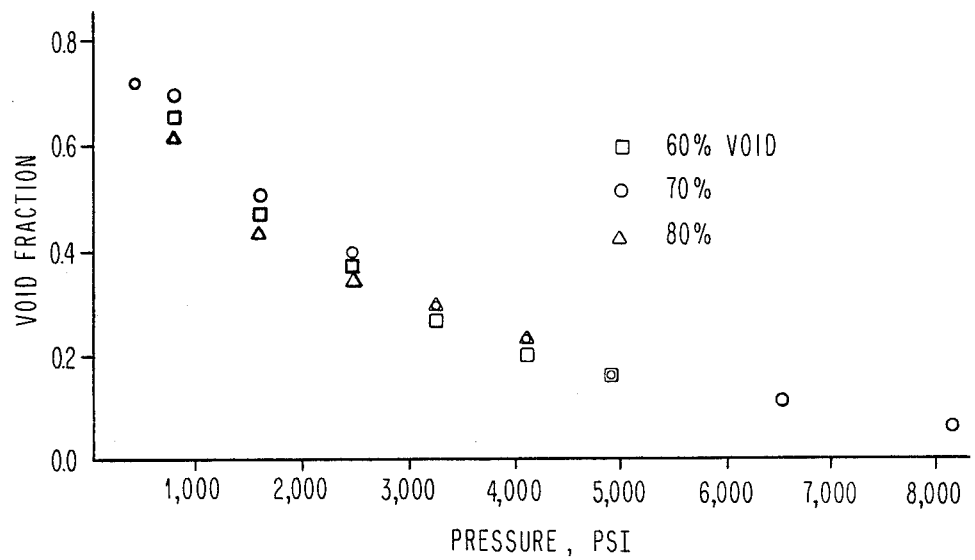
FIG. 2 is a graph showing the void fraction of the structures of the present invention made from three different microporous polypropylene powders, having void volumes of 60%, 70%, and 80%, respectively, as a function of the compressive force used to make the structures.

It is surprising that the relatively fragile microporous particles of the present invention can be formed into an integral structure having substantial physical integrity, which is simply sufficient strength to be handled, and that the structures retain a percentage of the original particle microporosity. It is especially surprising that a relatively strong solid composite structure results from the present invention, without the need for application of any external heat, solvent, binder, or other means for joining together the edges of the particles. It is furthermore surprising that when starting particles of different degrees of porosity (60% and 80%) are subjected to compression, the resulting void volume of the shaped article is practically only dependent on applied pressure. (FIG. 2).

Figure 3:
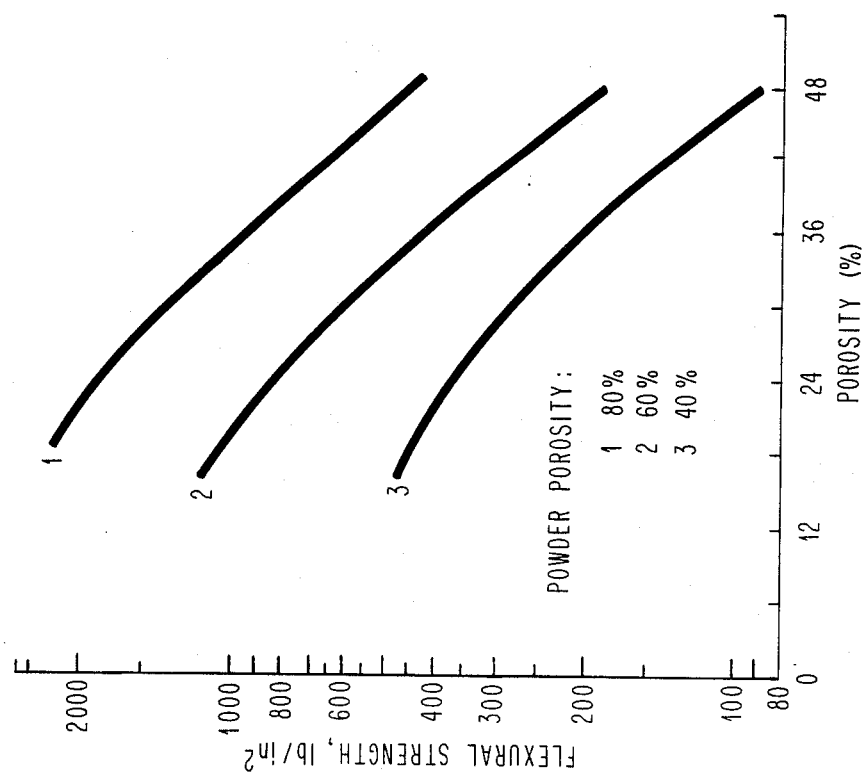
FIG. 3 is a graph showing the flexural strength of structures of the present invention made from microporous polypropylene powder, having void volumes of 60%, 70%, and 80%, respectively, as a function of the apparent porosity of the structures.

The mechanical strength of the articles, however, is heavily dependent on the starting porosity. Thus particles with 80% starting porosity yield a tablet of twice the strength obtained when particles with 60% starting porosity is used. (FIG. 3). Based on the foregoing, it appears that increasing starting microporosity provides increasing of binding forces and thus, increased strength in the compressed shaped article.

Figure 4:
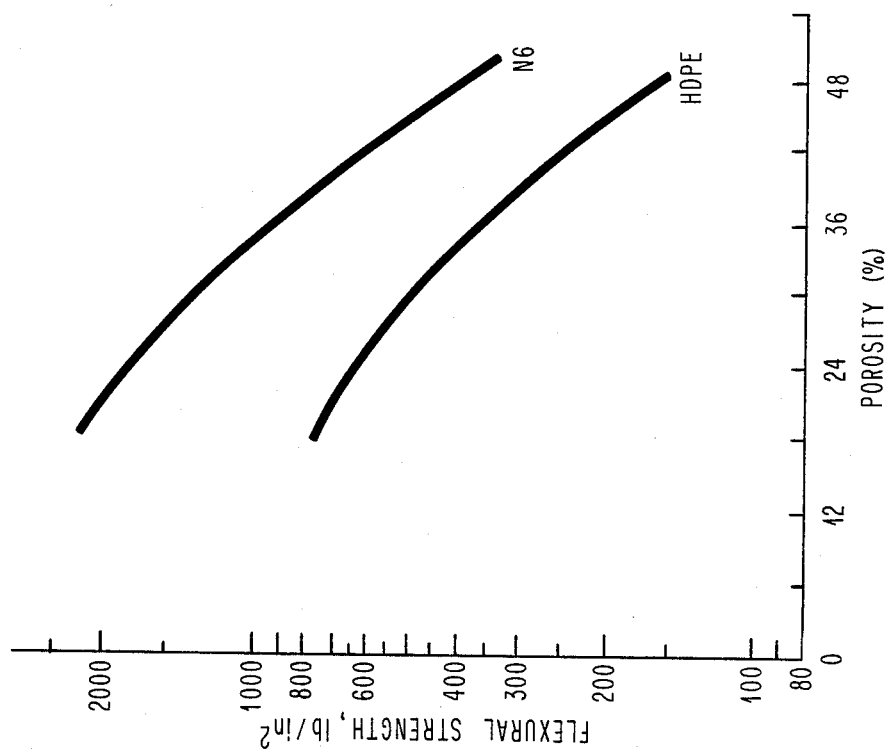
FIG. 4 is a graph comparing the flexural strength of structures of the present invention made from microporous nylon 6 and from high density polyethylene.

One would also expect that due to the different surface forces particles made from different polymers would produce structures of different strength at the same applied pressure, which indeed is found with polypropylene, nylon, and HDPE exhibiting decreasing strength in this order. (FIGS. 3 and 4).

Within the scope of the present invention it could be shown that the microporous particles may be loaded at least partially with an active ingredient such as a drug or medicinal and that such loaded particles which still contain the initial microporosity could be employed to make the desired structures. In such a manner it was possible to quickly load the particles as by soaking in a solution of the active ingredient and subsequently evaporating the solvent and then to subject the loaded particles to the compessive force to yield the integral structure containing the desired active ingredient. Such a method would obviate the need to soak the much larger structure in such a solution for prolonged periods to achieve the appropriate degree of penetration and then to subject the structure to an extensive drying period to evaporate the solvent. In another mode dye pigments could be added to the microporous polymer during the process as described in U.S. Pat. No. 4,247,498 and thus be incorporated in the compressed articles.

As discussed earlier the physical forces utilized for generating mechanical strength in the compressed article seem to be unique and result from the particular microporous structures.

Loading of said structures with certain active chemicals prior to the compression process does not significantly lower the cohesive surface forces utilized in the process. The present invention will be further described by the following nonlimiting examples.

EXAMPLE 1

Following the procedure of U.S. Pat. No. 4,247,498, a microporous solid was made from 25 percent, by weight, polypropylene and 75 percent, by weight, Armostat® 310 N,N-bis(2-hydroxyethyl)tallow amine. The resultant structure was cryogenically ground into microporous particles and then extracted with isopropanol to remove the amine, dried, and screened to remove any fines, so that the resultant particles were in a size range from about 40 to about 400 microns. Such particles are commercially available from Armak Company, Chicago, Ill., under the trademark Accurel® microporous powder.

The aforementioned powder was placed in a hydraulic press to form tablets of 3.175 cm diameter and a thickness between 4 and 8 mm, at indicated pressures from about 600 to about 3000 pounds, resulting in an effective pressure of about 500 to about 2450 pounds per square inch (psi). FIG. 1 shows the density of the resulting tablets versus the compression pressure in psi. All tablets had good mechanical strength and were easily handled without degradation of the product.

The density of the original microporous solid from which the microporous particles were made was about 0.225 g/cm$^3$ and the bulk density of the powder made therefrom was 0.147 g/cm$^3$.

It is well known that the most dense packing of spheres occurs in the hexagonal packing configuration and that in such a configuration 69% of the total volume of the pack is occupied by the spheres. Thus it would be expected that if all of the microporous particles were uniform and in a hexagonal packing configuration, the density of the powder would be 69% of the density of the particles themselves (0.225 g/cm$^3$), or 0.155 g/cm$^3$. Thus, the measured density was only about 5% less than the calculated theoretical, based upon hexagonal packing.

The density of the resultant structures obtained at the various applied pressures were as follows:

| APPLIED PRESSURE - lbs. (psi) | MEASURED DENSITY (g/cm$^3$) |
|---|---|
| 600 (500) | .3839 |
| 1200 (980) | .4953 |
| 1800 (1470) | .5808 |
| 2400 (1960) | .6121 |
| 3000 (2450) | .6408 |

Figure 5:
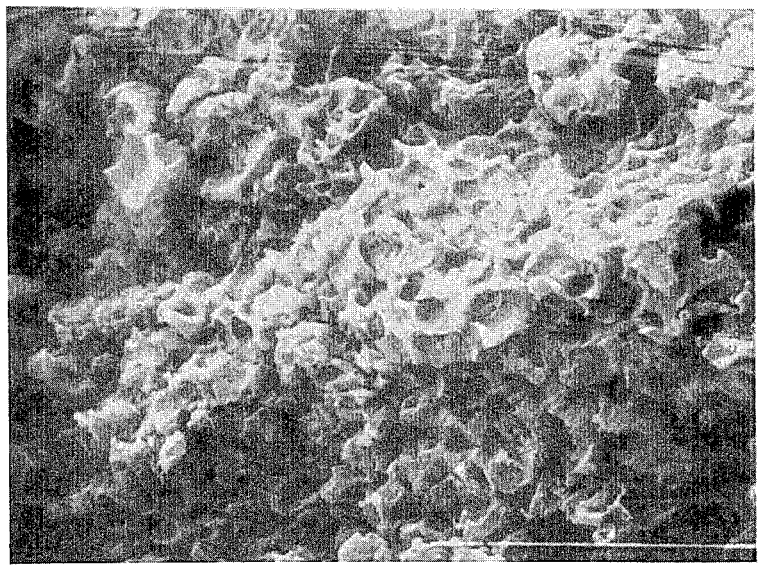
FIG. 5 is a Scanning Electron Photomicrograph at 1050× of a freeze-fracture of a product of the present invention showing that essentially no interstitial void space remains.

It is believed as pointed out above, that at compression forces below about 2450 psi the resultant structure has porosity mainly due to the original microporosity of the particles and less due to the interstitial space between the spheres. FIG. 5 is an SEM at 1050× of a freeze-fracture of a product obtained at an applied pressure of about 2000 lbs (1650 psi), showing that essentially no interstitial void space remains.

EXAMPLE 2

To demonstrate the mere application of pressure to particles of solid polypropylene only, such comparable particles were placed in the same hydraulic press and subjected to various pressures. Below about 2450 psi no coherent tablets could be formed and the edges were soft and shedded powder particles. At pressures from about 2450 to about 9800 psi the resulting structures had strengths and edges comparable to the tablets made in accordance with the present invention at levels of about 250 to about 500 psi. The density of the structures made with the solid particles of polypropylene were all approximated to be 0.7 g/cm$^3$.

Figure 6:
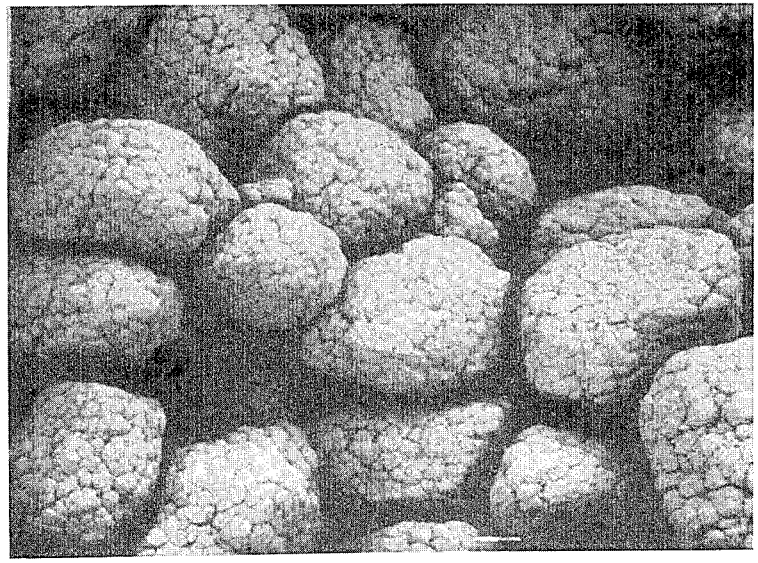
FIG. 6 is a Scanning Electron Photomicrograph at 1050× of a structure made from nonporous particles of solid polypropylene showing the presence of substantial interstitial void space and the flattening of the originally spherical particles.

Polypropylene has a density of 0.92/g/cm$^3$ so a theoretcal structure comprised of uniform spheres of solid polypropylene would be expected to have a density of 0.92 g/cm$^3$ × 0.69, or 0.63 g/cm$^3$. The small increase of density in the compressed objects is due to flattening of the orignally spherical surfaces as is evident from SEMs. FIG. 6 is a SEM at 105× of a freeze-fracture of a structure made at an applied pressure of about 10,000 lbs. (8,150 psi), showing the presence of substantial interstitial void space and the flattening of the originally spherical surfaces. Sufficient strength can only be achieved after flattening of the spherical solid particles in order to generate enough surface contact to provide cohesive forces. The strength of such products is still less than when microporous material is used at the same pressure.

EXAMPLE 3

Microporous polypropylene powder of 75% void volume made according to U.S. Pat. No. 4,247,498 was loaded with caffeine by soaking the powder at 55° C. in a 60/40 water/ethanol solution containing 8% dissolved caffeine. The solvent was removed by drying under vacuum at dry ice temperature. The dry powder containing 30% of its weight caffeine was compressed into a tablet as described in Example 1, applying 5000 psi. The tablet had good mechanical strength. The somewhat higher compression pressure fits well the aformentioned mechanical strength/void volume relation of FIG. 3. Similarly, Orasol Orange dye was loaded into powder and subsequently compressed into a disk.

EXAMPLE 4

A mixture of 700 g Armostat ® 310 amine, 50 g Inmont Red 17-73238 Liqui-Kolor ® (a 50% solids dispersion of red pigment in an oil vehicle), and 250 g polypropylene were heated to 200° C. until a uniform mixture was obtained. The mix was poured into a ¼" thick slab and was allowed to cool to room temperature. The slab was granulated, ground, and extracted with acetone to give a porous polymer powder containing approximately 9% pigment. The powder was compacted at 2500 psi in a die of 3.175 cm diameter by the sampe procedure in Example 1 to give tablets of comparable strength to a tablet made from unloaded microporous polypylene.

EXAMPLE 5

6% (w/w) of microporous polypropylene made according to U.S. Pat. No. 4,247,498 was mixed with 94% of solid polypropylene powder and compressed at 2000 psi. The resulting tablet showed excellent mechanical strength and no shedding of particles as observed in Example 2.

EXAMPLE 6

Microporous high density polyethylene particles of 75% void volume made according to U.S. Pat. No. 4,247,498, utilizing Armostat 310 amine as the compatible liquid, followed by cryogenic grinding and extraction, were placed in a hydraulic press to form tablets. Similarly microporous Nylon 6 particles of 80% void volume made according to U.S. Pat. No. 4,247,498, utilizing propylene carbonate as the compatible liquid, followed by cryogenic grinding, were placed in a hydraulic press to form tablets. FIG. 4 shows the flexural strength of the resultant structures as a fraction of their porosity. Nylon 6 structures as expected, exhibit a greater flexural strength than high density polyethylene structures but less than polypropylene structures based upon the same compressive force.

What is claimed is:

1. A method for making a microporous structure comprising forming a plurality of particles into a desired shape, said particles being in a size range from about 40 to about 400 microns and being comprised of from about 5 to about 100 percent by weight of microporous particles of a synthetic thermoplastic polymeric material and from about 0 to about 95 percent by weight of nonporous particles of a synthetic thermoplastic material and subjecting said particles to an effective pressure from about 200 to about 2500 pounds per square inch, without application of external heat, while retaining said particles in said desired shape, for a length of time sufficient to produce an integral microporous structure having substantial physical integrity.

2. The method of claim 1 wherein the microporous particles of a synthetic thermoplastic polymeric material and the nonporous particles of a synthetic thermoplastic material are independently selected from the group consisting of low density polyethylene, high density polyethylene, polypropylene, polystyrene, polyvinylchloride, acrylonitrile-butadiene-styrene terpolymers, styrene-acrylonitrile copolymer, styrene butadiene copolymers, poly(4-methyl-pentene-1), polybutylene, polyvinylidene chloride, polyvinyl butyral, chlorinated polyethylene, ethylene-vinyl acetate copolymers, polyvinyl acetate, and polyvinyl alcohol.

3. The method of claim 1 wherein the microporous particles of a synthetic thermoplastic polymeric material and the nonporous particles of a synthetic thermoplastic material are independently selected from the group consisting of polymethyl-methacrylate, polymethyl-acrylate, ethylene-acrylic acid copolymers, and ethylene-acrylic acid metal salt copolymers.

4. The method of claim 1 wherein the microporous particles of a synthetic thermoplastic polymeric material and the nonporous particles of a synthetic thermoplastic material are independently selected from the group consisting of polyphenylene oxide, polyethylene terephthalate, polybutylene terephthalate, Nylon 6, Nylon 11, Nylon 13, Nylon 66, polycarbonates and polysulfone.

5. The method of claim 1 wherein the microporous particles have a void volume of about 70 to about 80 percent.

6. The method of claim 5 wherein the particles have microporosity in the range from about 0.05 micron to about 5 microns.

7. The method of claim 1 wherein the microporous particles are loaded at least partially with an active ingredient.

8. The method of claim 7 wherein the active ingredient is a drug or medicinal.

9. The method of claim 6 further comprising loading the microporous particles with an active ingredient prior to forming the particles into the desired shape.

* * * * *